United States Patent [19]

Babb et al.

[11] Patent Number: 5,023,380

[45] Date of Patent: Jun. 11, 1991

[54] PERFLUOROVINYL COMPOUNDS

[75] Inventors: David A. Babb; Bobby R. Ezzell; Katherine S. Clement, all of Lake Jackson, Tex.

[73] Assignee: The Dow Chemical Company, Midland, Mich.

[21] Appl. No.: 364,665

[22] Filed: Jun. 9, 1989

[51] Int. Cl.$^5$ .................. C07C 315/00; C07C 317/00
[52] U.S. Cl. ....................... 568/34; 568/643; 568/649; 568/674; 568/573; 568/35; 568/36; 568/669; 560/87; 560/197; 560/219; 556/488; 532/1; 564/442; 564/509; 558/251; 558/230; 558/291
[58] Field of Search .................. 526/243; 528/86; 568/669, 3, 643, 649, 674, 57, 34, 35, 36; 525/276; 560/87, 197, 219; 558/251, 291, 230; 532/1; 564/442, 509; 556/488

[56] References Cited

U.S. PATENT DOCUMENTS

| | | |
|---|---|---|
| 2,404,374 | 10/1951 | Harmon . |
| 2,671,799 | 3/1954 | Miller . |
| 2,848,504 | 8/1958 | Dixon . |
| 2,922,823 | 7/1960 | Tarrant . |
| 2,958,685 | 11/1960 | Eleuterio . |
| 2,982,786 | 5/1961 | McCane . |
| 3,022,356 | 2/1962 | Nooy . |
| 3,111,509 | 11/1963 | Folt . |
| 3,277,068 | 10/1966 | Wall et al. . |
| 3,303,145 | 2/1967 | Carlson . |
| 3,316,312 | 4/1967 | McCane et al. . |
| 3,505,411 | 4/1970 | Rice . |
| 3,549,606 | 12/1970 | Gash . |
| 3,682,876 | 8/1972 | Anderson et al. . |
| 3,840,603 | 10/1974 | Anderson et al. . |
| 3,900,380 | 8/1975 | Anderson et al. . |
| 3,926,989 | 12/1975 | Rebsdat et al. . |
| 4,154,753 | 5/1979 | Fielding . |
| 4,377,711 | 3/1983 | Rico et al. . |
| 4,423,249 | 8/1983 | Carl et al. . |

OTHER PUBLICATIONS

Coffman, Barrick, Cramer and Raasch, in J. Amer. Chem. Soc., vol. 71 (1949), pp. 490–496.
Chemical Abstract 110:181626 of EP 293,856.
Henne and Ruh in J. Amer. Chem. Soc. 69, 279–281 (1947).
Maurice Prober in J. Amer. Chem. Soc., 75, 968–973 (1953).
Hauptschein et al., in J. Amer. Chem. Soc., 79, 2549–2553 (1957).
Miller et al., in J. Amer. Chem. Soc., 83, 1767–1768 (1961).
Brown et al., in J. Poly. Sci. Part A-1, vol. 3, (1965), pp. 1641–1660.
Brown et al., in J. Poly. Sci. Part A-1, vol. 34 (1966), pp. 131–1140.
Banks et al., in J. Chem. Soc. (C), 22 (1966), pp. 2051–2052.
Sharkey in Fluorine Chem. Rev. 2, 1–53 (1968).
Crawford in J. Chem. Soc. (C), 1967, pp. 2395–2396.
Hodgdon and MacDonald in J. Poly. Sci. Part A-1, vol. 6, (1968), pp. 711–717.
Chambers in Fluorine in Organic Chemistry, John Wiley, New York, (1973), pp. 173–191 and 199–208.
Rico and Waselman in J. Fluorine Chemistry, 20 (1982), 759–764.
Heinze and Burton in J. Org. Chem. 1988, 53, 2714–2720.

Primary Examiner—Lewis T. Jacobs
Assistant Examiner—Thomas McDonally

[57] ABSTRACT

Compounds have a structure represented by Formula I:

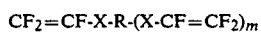

$$CF_2=CF-X-R-(X-CF=CF_2)_m$$

wherein R represents an unsubstituted or inertly substituted hydrocarbyl group; each X is independently selected from the group consisting of groups having at least one non-carbon atom between R and $-CF=CF_2$; and m is an integer of from 1 to about 3. Polymers formed from such compounds are also prepared. The compounds are preferably prepared by a method by a process comprising the steps of:

(a) forming a salt having anion corresponding to a compound of Formula II:

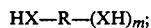

$$HX-R-(XH)_m;$$

wherein X, R and m are as defined for Formula I;
(b) reacting the salt with a 1,2-dihalo-1,1,2, 2-tetrafluoroethane wherein the halo groups are iodine, bromine, chlorine or mixtures thereof, at least one halo group being bromine or iodine, to form a compound of Formula III:

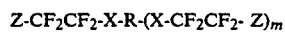

$$Z-CF_2CF_2-X-R-(X-CF_2CF_2-Z)_m$$

wherein X, R and m are as defined for Formula I and each Z is independently iodine or bromine;
(c) eliminating the halogen atoms represented by Z to form the perfluorovinyl compound represented by Formula I.

9 Claims, No Drawings

PERFLUOROVINYL COMPOUNDS

This invention relates to compounds having at least two perfluorovinyl groups and to their preparation and polymerization.

Certain compounds having a perfluorovinyl group have been prepared by a variety of methods such as those disclosed in U.S. Pat. No. 2,671,799 to Miller: U.S. Pat. No. 3,277,068 to Wall et al.; Prober in *J. Amer. Chem Soc.* v. 75 (1953) pp. 968-973: Hodgdon and Macdonald, *J. Polymer Sci.* Part A-1, v. 6 (1968) pp. 711-717: Heinze and Burton, *J. Org. Chem.* 1988, 53, 2714-2720 and references cited in these references.

Certain alkyl or aryl 1,1-difluoroalkyl ethers such as 1,1,2-trifluoro-2-chloro-2-iodoethyl phenyl ether are prepared by reacting an alkoxide or phenoxide with certain 1,1-difluoro-1,2-dihaloethanes under conditions disclosed in U.S. Pat. No. 4,423,249 to Carl and Ezzell. In the same reference certain of the 1,1-difluoroalkyl ethers are disclosed to be dehalogenated using zinc to form the corresponding vinyl ethers.

SUMMARY OF THE INVENTION

In one aspect the invention is a compound having a structure represented by Formula I:

$$CF_2=CF-X-R-(X-CF=CF_2)_m$$

wherein R represents an unsubstituted or inertly substituted hydrocarbyl group; each X is independently selected from the group consisting of oxygen atoms, sulfur atoms, sulfoxide, sulfone, carbonyl, thiocarbonyl and silanediyl groups: and m is an integer of from 1 to about 3.

In yet another aspect, the invention is a method of preparing compounds of Formula I:

$$CF_2=CF-X-R-(X-CF=CF_2)_m$$

wherein each X is independently —O—, —S—, —SO$_2$— or —SO—; and R is a hydrocarbyl group, which group is unsubstituted or inertly substituted, by a process comprising the steps of:

(a) forming a salt having anion corresponding to a compound of Formula II:

$$HX-R-(XH)_m;$$

wherein X, R and m are as defined for Formula I, (b) reacting the salt with a 1,2-dihalo-1,1,2, 2-tetrafluoroethane wherein the halo groups are iodine, bromine, chlorine or mixtures thereof, at least one halo group being bromine or iodine to form a compound of Formula III:

$$Z-CF_2CF_2-X-R-(X-CF_2CF_2-Z)_m$$

wherein X, R, and m are as defined for Formula I, and each Z is independently iodine or bromine:

(c) eliminating the halogen atoms represented by Z to form the perfluorovinyl compound represented by Formula I.

In yet another aspect, the invention includes polymers of compounds of Formula I.

DETAILED DESCRIPTION OF THE INVENTION

The monomers preferably have a structure represented by Formula I:

$$CF_2=CF-X-R-(X-CF=CF_2)_m$$

wherein R represents an, optionally inertly substituted, hydrocarbyl group; each X is independently a bond or any group which links R and a perfluorovinyl group (hereinafter linking structures), said structures being inert; m+1 is the number of —X—CF=CF$_2$ units. Advantageously, m is an integer of from about 1 to about 3, preferably from about 1 to about 2. By "inert" it is meant that the structures or substituents do not react undesirably with perfluorovinyl groups or interfere undesirably with polymerization (perfluorocyclobutane formation) of the monomers.

Linking structures X are each independently a linking structure such as a bond, an oxygen atom, carboxylic and thiocarboxylic ester groups, other sulfur containing structures, perfluoroalkylene, perfluoroalkylene ether, alkylene, acetylene, phosphorus containing groups such as phosphines, carbonyl and thio carbonyl groups: seleno; telluro; nitrido; silicon-containing groups such as silanediyl, trisilanediyl tetrasilanetetrayl, siloxanediyl, disiloxanediyl, trisiloxyl, trisilazanyl, or silylthio groups; boron-containing groups such as boranediyl or methylboranediyl groups; a combination thereof, or any other group which is inert, which molecularly links R to a perfluorovinyl group, and which provides a molecular structure in which the perfluorovinyl group is sufficiently reactive to form a perfluorocyclobutane ring. For instance, X is preferably other than a perfluoroalkylene groups because perfluorovinyl groups attached to perfluoroalkylene groups generally require temperatures greater than about 300° C. to dimerize and are subject to isomerization.

It is preferred that at least one of X is not a bond. More preferably, X is independently selected from the group consisting of groups having at least one noncarbon atom between the perfluorovinyl groups and R, such as groups containing oxygen, sulfur, selenium atoms, tellurium atoms, silicon, boron, phosphorus or nitrogen between R and the perfluorovinyl group, e.g. oxygen atoms, sulfur atoms, (thio) carboxylic ester groups, phosphines, (thio) carbonyl groups, seleno, telluro, silanediyl, trisilanediyl, trisilazanyl or silylthio, boranediyl groups. Preferred groups have S, O, Si, N or P, more preferably S, O, or Si between R and the perfluorovinyl group, such as carbonyl, thiocarbonyl, sulfone, sulfoxy, silanediyl, amines (optionally inertly substituted), oxygen or sulfur atoms. Most preferably X is a single atom other than carbon; even more preferably it is oxygen or sulfur, among those groups preferably an ether or sulfide linkage, because monomers having such linking structures advantageously form perfluorocyclobutane groups at lower temperatures than are needed with such groups as perfluoroalkyl groups and are more stable than monomers where the perfluorovinyl group is attached directly to R, particularly when R is aromatic. Monomers having such linking structures are also relatively easily prepared.

R is suitably any inert hydrocarbyl molecular structure, preferably a molecular structure which facilitates formation of perfluorocyclobutane rings and/or imparts desirable physical properties to polymers or oligomers prepared from the monomers. For the purpose of imparting desirable physical properties to polymers, R preferably contains at least one carbon atom. Preferably, the carbon atom is in the molecular chain between X's because monomers having at least one carbon atom between X's when each X is other than a bond, tend to have desirable stability and to produce polymers having desirable physical properties. Alternatively, the carbon atom is in a side chain; for instance, —R— can be —N(CH$_3$)—, —N(CH$_2$CH$_3$)— —P(CH$_3$)—, P(CH$_2$CH$_3$)— and the like. The carbon atoms(s) in R are suitably in aliphatic, cycloaliphatic, aromatic, heterocyclic groups and the like and combinations thereof. R is preferably a hydrocarbyl group, that is a group containing at least one carbon hydrogen bond, for instance a methylene group, a phenylene group, a pyridinyl group and the like. Additionally, R optionally contains groups or has substituents which are inert, that is which do not undesirably interfere with the formation of perfluorocyclobutane rings from perfluorovinyl groups. Inert substituents include ether, carbonyl, ester, tertiary amide, carbonate, sulfide, sulfoxide, sulfone, nitrile, alkyl phosphonate, tertiary amine, alkyl phosphate, alkyl silyl, chlorine, bromine, fluorine, alkyl, arylalkyl, alkylaryl, cycloalkyl, aromatic, heterocyclic, alkoxyl, aryloxy groups and the like, which inert substituents are suitably in any position, for instance, in a polymer backbone between X's and/or appended to such a backbone. Carbon-containing inert substituents on R preferably contain from about 1 to about 50, more preferably from about 1 to about 12 carbon atoms because of the stability and ease of working with monomers of lower molecular weight. R, including inert substituents preferably has a molecular weight (MW) of from about 14 to about 20,000, more preferably from about 75 to about 15,000 and most preferably from about 75 to about 5,000. These ranges include monomeric and oligomeric R groups. In the case of monomers which are other than oligomeric, R preferably has from about 1 to about 50, more preferably from about 6 to about 25, carbon atoms because molecular weights above this reduce the contribution to properties made by the fluorine-containing substituents. The nature of R as well as the perfluorocyclobutane content of the polymers can vary broadly according to the type of products desired.

Preferably, for polymers having good plastic properties such as tensile strength and flexibility, at least one carbon atom of R is in the molecular chain between X's and is part of an aromatic nucleus. Aromatic groups are desirable because of improved physical properties of the polymers and ease of manufacture of the monomers. For both ease of manufacture of the monomer and monomer stability, when R is aromatic, each X is preferably independently sulfur or oxygen. The aromatic group can be any molecular structure having aromatic character, advantageously having at least one six membered aromatic ring, suitably having any number of such six-membered rings fused together or connected by bonds or linking structures. R preferably has from about 1 to about 50 such rings, more preferably from about 1 to about 10 rings, more preferably containing from about 6 to about 25 carbon atoms, most preferably R has at least 2 to about 4 aromatic rings to impart properties such as hardness and/or stiffness to a polymer. The aromatic fragment is suitably unsubstituted or inertly substituted. Inert substituents on an aromatic R include, for instance, the inert substituents listed for R generally. Exemplary aromatic molecular fragments include, for instance, perchlorophenylene, phenylene, biphenylene, naphthylene, dichlorophenylene, nitrophenylene, p,p'(2,2-diphenylene propane) [—C$_6$H$_4$—C(CH$_3$)$_2$—C$_6$H$_4$]; p,p'-(2,2-diphenylene-1,1,1,3,3,3 hexafluoropropane) [—C$_6$H$_4$—C(CF$_3$)$_2$—C$_6$H$_4$], preferably biphenylene; phenylene; 9,9'-diphenylfluorene, oxydiphenylene: thiodiphenylene: 2,2-diphenylene propane: 2,2'-diphenylene, 1,1,1,3,3,3-hexafluoropropane; 1,1-diphenylene-1-phenyl ethane: naphthalene; and anthracene. Molecular weights of aromatic ring containing polymers are preferably at least about 10,000. Such aromatic groups are preferably present because they generally impart high temperature glass transition properties (Tg) and good mechanical strength (e.g. as measured by differential scanning calorimetry (DSC) and tensile/flexural tests) to the polymer.

Most preferably, at least one aromatic carbon atom of R is bonded directly to X, most preferably aromatic carbon atoms of R are bonded directly to each X because perfluorovinyl groups bonded to X, said X being bonded to aromatic groups are generally more reactive in forming perfluorocyclobutane rings.

Some specific combinations of X and R are especially preferred: when R is aromatic, at least one X is preferably other than a bond, more preferably neither X is a bond because attachment of perfluorovinyl groups directly to aromatic R renders the perfluorovinyl groups more thermally and oxidatively unstable than when said groups are attached, for instance to oxygen or sulfur.

Monomers useful in the practice of the invention are suitably prepared by any method which links molecular structures having perfluorovinyl groups to other molecular structures or which form perfluorovinyl groups. A variety of methods of preparation are suitable and are taught, for instance in copending U.S. applications Ser. No. 364,667 filed June 9, 1989 pending, and Ser. No. 364,666 filed June 9, 1989 pending which are incorporated herein by reference.

Compounds of Formula I are preferably formed by a process comprising the steps of:
(a) forming a salt having an anion corresponding to a compound of Formula II:

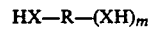

HX—R—(XH)$_m$ wherein R, X and m are defined as for Formula I:
(b) reacting the salt with a 1,2-dihalo-1,1,2, 2-tetrafluoroethane wherein the halo groups are iodine, bromine, chlorine or mixtures thereof, at least one halo group being a bromine or an iodine atom, to form a compound of Formula III:

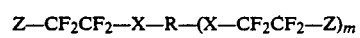

Z—CF$_2$CF$_2$—X—R—(X—CF$_2$CF$_2$—Z)$_m$ wherein R, X and m are defined as for Formula 1; and each Z is independently iodine or bromine;
(c) eliminating the halogen atoms represented by Z to form the perfluorovinyl compound.

Salts of compounds of Formula II

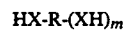

HX-R-(XH)$_m$ wherein R, X and m are as defined for Formula I; are suitably formed by any method which replaces the hydrogen atoms with metal cations. Suitable methods include reaction with bases such as sodium hydroxide or potassium hydroxide when the compound has an acidity sufficiently high to react with a hydroxides, such as when R is aromatic or aromatic heterocyclic. Compounds of lower acidity are reacted, for instance, with metals such as sodium or their hydrides. Among hydroxides, potassium hydroxide is generally preferred because potassium salts of alkoxides or aryloxides are more reactive than are lithium or sodium salts. For instance, sufficient hydroxide or metal to form the salt is used, preferably from about 1.0 to about 2.0 equivalents of hydroxide of metal per equivalent of X in compounds of Formula II. Suitable temperatures and pressures are determined without undue experimentation and are conveniently atmospheric pressure and a temperature maintained below about 140° C. because oxidative degradation of some air-sensitive aryl oxides is enhanced at higher temperatures. Temperatures are preferably from about 40° C. to about 125° C. for an aromatic compound (R is aromatic) and of from about $-10°$ C. to about 125° C. for an alkyl compound.

Suitably, both the compound of Formula II and the hydroxide are slurried or dissolved in an easily removeable medium such as methanol before reaction for ease of mixing the reactants. Alternatively, and preferably the hydroxide is mixed directly into a solution of the compound of Formula II in a solvent such as dimethylsulfoxide (DMSO) or dimethylformamide (DMF).

Alternatively, salts may be formed by reaction of compounds of Formula 11 with metals such as sodium or potassium or any metal which forms metal salts with compounds of Formula II; or with the metal salts of carbon acids such as the sodium salt of DMSO or the potassium salt of dimethylsulfone, preferably at temperatures of from about $-20°$ C. to about 200° C. These reactions are particularly useful when R is alkyl or substituted alkyl. Use of metals is within the skill in the art and is found, for instance in Introduction to Organic Chemistry, A. Streitwieser, Jr. and C. H. Heathcock, Macmillan Publishing Co., New York 1976, p. 216. Use of metal salts of carbon acids is detailed in W. S. Matthews, et. al. *J. Amer. Chem. Soc.* 97:24 pages 7006-7014 (1975), which is incorporated herein by reference.

Although it is generally preferable for convenience, to maintain reactants in a slurry or solution for subsequent reaction, any liquid media, e.g. methanol or glyme is suitably, alternatively, removed before the next reaction step. Removal of protic media is necessary and removal is within the skill in the art. Methanol, for instance is conveniently removed by rotary evaporation followed by heating to about 100°-140° C. under vacuum until the salt is dry.

The salt is then reacted with a 1,2-dihalo-1,1,2,2-tetrafluoroethane which is commercially available, or is prepared by reacting a halogen such as bromine or iodine with tetrafluoroethylene. The dihalotetrafloroethane has a structure represented by Formula IV:

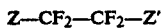

Z—CF$_2$—CF$_2$—Z' wherein Z and Z' represent halogens other than fluorine. Z and Z' are preferably selected such that the tetrafluoroethane reacts readily with the anion leaving one halogen Z or Z', and that halogen is later readily eliminated to form a perfluorovinyl group. Z and Z' are, therefore, preferably selected from Cl, Br, and I wherein at least one of Z or Z' is bromine or iodine: more preferably both Z and Z' are Br or I; most preferably both are Br. 1,2-dibromo-1,1,2,2-tetrafluoroethane is preferred because it is readily available and undergoes elimination readily under suitable conditions.

The 1,2-dihalo tetrafluoroethane is preferably reacted with the salt in a liquid reaction medium which is, for instance, suitably a solution or slurry of the salt in an aprotic solvent such as dioxane, dimethyl sulfoxide (DMSO), glyme, diglyme, tetraglyme, tetrahydrofuran, dimethylformamide or acetonitrile. Polar aprotic solvents are preferred, with DMSO most preferred when the salt form of compounds of Formula II have low solubility. When the reaction medium is a slurry it is preferably stirred sufficiently to maintain the slurry and contact between the dihalo-tetrafluoroethane and the salt. Sufficient solvent to homogeneously disperse both the dihalo-tetrafluoroethane and the salt is used, preferably from about 0.01M to about 10M concentration of salt of Formula II to use for convenience. Sufficient salt is reacted with the dihalotetrafluoroethane to form a predetermined degree of substitution; preferably from about 0.1 to about 10.0 moles of salt per mole of dihalotetrafluoroethane is supplied, more preferably from about 0.30 to about 1.1 mole of salt. The dihalotetrafluoroethane is preferably added as a liquid.

The reaction temperature is preferably maintained above $-30°$ C. to achieve reaction at a convenient rate and below 100° C. to avoid by-products. More preferably the temperature is maintained between about 0° C. and about 50° C., most preferably between about 20° C. and about 40° C. when R is aromatic and each X is independently —O—, —S—, —SO$_2$— or —SO—; most preferably between about 0° C. and about 20° C. when R is alkyl. These temperatures are preferably used at atmospheric pressure which is preferably used for convenience. Alternatively sub- or super-atmospheric pressure is used and temperature adjustments within the skill in the art are made. The temperature of the reaction is also dependent on the nature of any substituent group. In general, electron donating substituents enhance the reaction, and cooling is necessary to keep the reaction temperature down. Electron donating substituents also activate the aromatic ring toward halogenation which can be a significant side reaction at elevated temperatures. The reactions are preferably run at the lowest temperature possible to prevent ring halogenation. Electron withdrawing substituents, however, retard the reaction and deactivate the ring toward halogenation. Reactions involving deactivated phenols must be heated to obtain a reasonable reaction rate. These can be heated much hotter than the activated phenols, since the deactivating groups also retard ring halogenation. In all cases the reaction is kept substantially free of protic materials, which are preferably at concentrations of less than about 0.1 weight percent, most preferably in no detectable concentrations. Protic materials cause the production of an undesirable side product (i.e. —OCF$_2$CF$_2$H instead of —OCF$_2$CF$_2$Br). Protic materials include water, alcohols, phenols and the like.

The reaction of the salt and the 1,2-dihalotetrafluoroethane forms a 2-halo-tetrafluoroethyl compound of Formula III. The 2-halo-tetrafluoroethyl compound is either separated from the liquid media or further reacted in the media. Removal is by means within the skill in the art, such as by pouring the slurry into an equal volume of water and removing the product in a lower, oily layer which is then purified by vacuum distillation. If a liquid medium such as tetraglyme which does not dissolve completely in water is used, the product is conveniently distilled therefrom under vacuum. Otherwise the solvent may be evaporated from the product as by heating under vacuum on a rotary evaporator. Purification of the 2-halotetrafluoroethyl compound is advantageous to subsequent reactions.

The non-fluorine halogen atom and one fluorine atom are then eliminated from the product 2-halotetrafluoroethyl compound to form the perfluorovinyl compound. The elimination is suitably conducted by any effective means. Preferably a metallic reagent such as zinc or magnesium is reacted with the 2-halotetrafluoroethyl compound, preferably in a liquid medium such as the ones suitable for formation of the salt. Alternatively, some reactants are sufficiently liquid for convenient reaction without solvent. More preferably, the 2-halotetrafluoroethyl compound is added to a hot, about 40° C.–150° C., slurry of (preferably granular) zinc most preferably in a dry glyme, or other liquid media which promotes the elimination reaction. The reaction is exothermic and the temperature is regulated by the speed of the addition of reactants. Most preferably, the halotetrafluoroethyl compound is mixed with the metallic reagent in a dry glyme and heated at about 85°–135° C. with stirring until the perfluorovinyl compound is formed, generally several hours, conveniently overnight.

After completion of the reaction, any precipitated materials, e.g. metal salts are removed by methods within the skill in the art, conveniently by centrifugation. If glyme or a lower boiling solvent is used, the solvent is conveniently removed by rotary evaporation and the product is preferably purified by vacuum distillation. Otherwise, purification means within the skill in the art, such as fractional distillation are used.

Such preparations yield compounds of the invention having at least two perfluorovinyl groups. The perfluorovinyl groups are thermally reacted to form perfluorocyclobutane rings which link the compounds into polymers.

Polymers produced from the preferred monomers, advantageously have a formula represented by Formula II:

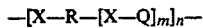

wherein R, X, and m, are defined above, Q is a perfluorocyclobutane group; and n is an integer representing the number of repeating units, which is preferably from about 2 to about 100,000. More preferably from about 2 to about 10,000, most preferably from about 3 to about 5,000. More preferably m is one or two. Formula II is generalized; when m is greater than one, some of the —X—Q— structures represent branching and/or cross-linking.

The monomers are heated to a temperature and for a time sufficient to form perfluorocyclobutane rings. Temperatures suitable for forming perfluorocyclobutane rings differ with the structure of the monomer. In general, temperatures above about 40° C. are suitable for formation of perfluorocyclobutane rings, preferably the temperature is above about 50° C., more preferably above about 100° C., because these temperatures result in formation of the rings at successively faster rates. Temperatures above about 450° C. are preferably avoided because perfluorocyclobutane groups are generally thermally unstable above such temperatures. Most preferably a temperature of from about 105° C. to about 350° C., most preferably from about 105° C. to about 250° C., is used to produce the perfluorocyclobutane rings at a convenient rate. Within that range, a temperature of from about 100° to about 230° is generally most preferred for cyclization of perfluorovinyl aromatic or aliphatic ethers or sulfides, while a temperature of from about 50° C. to 80° C. is needed to form perfluorocyclobutane groups when the perfluorovinyl group is attached directly to an aromatic ring. In the case of perfluoroalkylperfluorovinyl groups, however, temperature at least about 300° C., preferably at least about 350° C., are generally required.

Preferably, especially when the perfluorovinyl compounds are capable of addition polymerization, conditions conducive to free radical polymerization, e.g. presence of oxygen, ozone, peroxygen compounds and other free radical generating compounds are avoided so that the perfluorovinyl groups will dimerize into perfluorocyclobutane groups rather than undergoing addition polymerization. Compounds known in the art for stabilization against free radical polymerization are alternatively used. Similarly, especially when the perfluorovinyl groups are capable of addition polymerization in the presence of anions or cations, compounds which supply such anions or cations are avoided. For instance, fluoride ions (e.g. from carbonyl fluorides) chloride, hydroxide, phenoxide and the like are preferably avoided. To avoid such compounds as carbonyl fluorides, oxidative conditions such as presence of oxygen, hypochlorite, dichromate, permanganate and the like are preferably avoided because perfluorovinyl groups are known to oxidize to form carbonyl fluorides.

Monomers or admixtures thereof are suitably neat or, optionally, in admixture with other materials such as in solution, in emulsion, in dispersions or in any other form in which monomer molecules can be contacted with one another to form a polymer. Liquid admixtures are advantageous for maintaining contact between monomer molecules such that higher molecular weight polymers are formed. This is particularly useful when linear thermoplastic polymers are the products. Neat polymerization is preferred when the monomers or prepolymers are formed in the final desired shape of the polymer article. This is especially true when monomers having more than two perfluorovinyl groups are used in whole or in part to formed crosslinked, thermoset materials. Neat polymerizations or oligomerizations are also generally preferred to form relatively low molecular weight fluid products.

Suitable solvents are those which are inert to the conditions encountered in the polymerization reaction and include perfluorotetradecahydrophenanthrene (MULTIFLUOR ® APF 215 commercially available from Air Products Corp.). At atmospheric pressure preferred solvents are those which attain temperatures of 170°–250° C. such as dichlorobenzene, trichlorobenzene, diphenyl oxide and perfluorotetradecahydrophenanthrene. Although solvents such as 1,2-dichlorobenzene and 1,2,4-trichlorobenzene give less satisfactory results such as discoloration of the finished polymer, they are suitably used when their disadvantages are tolerable in a final product. When a solvent is used the concentration of monomers in solvent is advantageously from about 0.1 molar to about 99.9M weight percents preferably, from about 10 to about 90 percent by weight monomer.

Polymerization or dimerization suitably takes place at any pressure. Pressures are generally chosen such that the monomers and any solvents and/or dispersing media remain liquid at the temperatures used for polymerization. When the monomers or other materials evaporate at temperatures used, then it is generally preferable to maintain a pressure at least sufficient to maintain the materials liquid.

Additional detail regarding these polymerization processes are found in copending U.S application Ser. No. 364,667 filed June 9, 1989 pending simultaneously herewith which is incorporated by reference herein in its entirety.

All gas chromatography/mass spectrometry (GC/MS) analyses of monomers and intermediates are performed on a Finnigan 1020 GC/MS using a 30 meter RSL-150 fused silica capillary column. All gas chromatography/mass spectrometry (GC/MS) analyses of fluid polymer samples are performed on a Finnigan 4500 GC/MS using a 60 meter DB-1 fused silica capillary column, with the GC program run at 290° C. isothermal. Liquid chromatography/mass spectrometry (LC/MS) is performed on a Finnigan 4500 mass spectrometer using acetonitrile—water eluent and a moving belt LC/MS interface.

Dynamic Mechanical Spectroscopy (DMS) measurements are performed on a Rheometrics RDS-7700 rheometer in torsional rectangular geometry mode using 60 mm × 12 mm × 3 mm samples at 0.05% strain and 1 Hz. Differential scanning calorimetry (DSC) is performed on a Perkin Elmer 7000 thermal analysis system scanning from ambient temperature to 350° C. at 20° C. per minute.

Dielectric constant and dissipation factor measurements are conducted according to the procedures of ASTM D150-87. Tensile strength and modulus and percent elongation were measured on an Instron model 1125 according to the procedures of ASTM D-882-83.

Gel Permeation Chromatography (GPC) is performed on a Waters 720 GPC instrument using a methylene chloride eluent and a series of Microstyragel® columns of 10,000, 1,000, 500 and 100 angstrom pore sizes. Reported values are standardized against polystyrene.

Granular zinc is activated by washing in 0.1N hydrochloric acid (HCl) followed by drying in a vacuum oven at 0.5 torr and 140° C. for 10 hours.

Infrared (IR) spectra are measured on a Beckmann Microlab 600 model spectrophotometer. Nuclear Magnetic Resonance (NMR) spectra are measured on a Varian EM360 spectrometer using 19F (fluorine 19) or 1H (hydrogen) mode.

EXAMPLE 1

Preparation and Bulk Polymerization of 4,4'-Bis(Trifluorovinyloxy)Biphenyl

Dimethyl sulfoxide (DMSO) (1800 ml) is placed in a 5-liter 5-necked flask fitted with a mechanical stirrer, a Dean-Stark phase separating trap topped with a nitrogen padded reflux condenser, and a thermocouple attached to a temperature controller. The solvent is stirred and purged of oxygen by blowing in nitrogen through a dip-tube placed below the surface of the liquid while 4,4'-dihydroxybiphenyl (454 g, 2.44 mole) is added to the flask.

The system is stirred and purged for 20 minutes, then potassium hydroxide (85% pellets) (322 g, 4.88 mole) is added slowly. The stirred mixture is then heated to 120° C. The temperature is held at 120° C. for 1.5 hours, then the heat is turned off and the mixture is allowed to cool to room temperature. Toluene (600 ml) which has been thoroughly purged with nitrogen is added to the solution and the resulting mixture is heated to reflux (135° C.). Water is azeotropically removed from the reactor through the Dean-Stark trap for a total of 4 days, cooling the reactor once after 24 hours to allow for salt formation to be broken up by opening the flask under a nitrogen sweep and scraping the sides with a spatula. After 4 days the Dean-Stark trap is removed and replaced with a Soxhlet extractor containing anhydrous sodium sulfate. The toluene is then refluxed through the Soxhlet extractor for 7 hours to dry the toluene. After 7 hours, the Soxhlet is replaced with a Dean-Stark trap, and toluene (300 ml) is removed from the reactor by simple distillation. The reaction mixture is then cooled to 30° C. in an ice water bath and 1,2-dibromotetrafluoroethane (1300 g, 5.00 mole) is added slowly dropwise over three hours at a rate that maintains a reactor temperature of 35°±2° C. When the addition is complete the reaction temperature is allowed to stabilize (not increasing in temperature when the ice bath is removed) and then a heating mantle is applied to the flask. The reactor is heated to 50° C. for 8 hours, then allowed to cool to room temperature with constant stirring. The crude reaction mixture is filtered to remove the potassium bromide salts, and the precipitate is washed with acetone. The filtrates are combined and thoroughly evaporated to remove acetone, DMSO and residual toluene. The solid residue is subjected to a 2 liter Kugelrohr bulb-to-bulb distillation to provide the crude product. This material is dissolved in 750 ml of methylene chloride and is washed first with mild aqueous potassium bicarbonate (500 ml, approximately. 0.2M), then with mild aqueous hydrochloric acid (HCl) (500 ml, approximately 0.05M), then twice with distilled water (500 ml each). After complete phase separation the product layer is removed and evaporated, and the residue is fractionally distilled (138°–148° C., 0.35 torr) to provide 1031.1 g (1.90 mole, 77.9% yield) of 4,4'-bis(2-bromotetrafluoroethoxy)biphenyl, melting point 71°–73° C. The Infrared (IR) spectra of the product has the following peaks (cm$^{-1}$): 1601,1492 (indicating an aromatic double bond): 1199-1107 (indicating carbon-oxygen and carbon fluorine bonds): 842, 788 (indicating aromatic character). The gas chromatograph/mass spectrometer (GC/MS) indicates peaks at the following mass to charge ratios: (m/e)=545 (29.8%); 543 (48.9%); 541 (23.8%): 365 (48.7%): 363 (50.9%); 337 (30.3%); 335 (34.7%): 168 (33.7%): 156 (78.3%): 140 (36.7%); 139 (90.1%); 129 (37.4%); 128 (100.0%); 127 (33.2%); 102 (32.9%): 76 (41.1%); 63 (34.3%), consistent with a product of 4,4'-bis(2-bromotetrafluoroethoxy)biphenyl.

Bromine is eliminated from this product by the followng procedure:

Into a 1-liter 5-necked flask equipped with a mechanical stirrer, a thermocouple attached to a temperature controller, a powder addition funnel and a reflux condenser, is placed freshly distilled diglyme (200 ml) and fresh zinc powder (36.0 g, 0.55 mole).

The mixture is stirred and heated to 130° C. Powdered 4,4'-bis(2-bromotetrafluoroethoxy)biphenyl (100 g, 0.184 mole) is added very slowly via the powder addition funnel over 3.5 hours. The mixture is then stirred mechanically at 115° C. for 1 hour, after which, heating is turned off and the mixture is allowed to cool to room temperature. The solution is centrifuged to remove the zinc salts. Then the liquid is decanted, and the zinc salts are washed with acetone and centrifuged again. The liquid portions are combined and evaporated thoroughly, and the residue is dissolved in methylene chloride and washed with 0.05M hydrochloric acid.

The methylene chloride solution is evaporated to provide 62.45 g (0.180 mole) of 4,4'-bis(trifluorovinyloxy)-biphenyl of 94.5% purity in 98% yield.

The product is then recrystallized in an ethanol/water mixture to give product of 99.8% purity in greater than 70% recovery, melting point 44°-46° C.

The IR spectrum shows peaks at (cm$^{-1}$): 1833 (indicative of a perfluorovinyl group); 1601,1491 (indicative of an aromatic double bond); 1231, 1196-1132 (indicative of carbon-oxygen and carbon-fluorine bonds respectively); 818 (indicative of aromaticity).

The GC/MS spectrum has the following peaks: m/e: 346 (31.3%); 153 (13.8%); 152 (100.0%): 151 (27.0%): 150 (11.7%): 76 (14.9%); 63 (14.9%).

Differential scanning calorimetry (DSC) analysis of the 4,4'-bis(trifluorovinyloxy)biphenyl monomer (20° C. to 360° C. at 20° C./minute) indicates a sharp endotherm of melting beginning at 45° C., followed by a broad exotherm beginning at about 170° C., interpreted as corresponding to the heat of cyclization of the trifluorovinyl groups to form hexafluorocyclobutane rings.

The monomer, 4,4'-bis(trifluorovinyloxy)biphenyl, (15.0 g, 0.043 mole) is placed in a nitrogen purged 100 ml round bottom flask and polymerized by heating at 210° C. for 2 hours without stirring. After cooling, a small sample is removed for analysis by differential scanning calorimetry (DSC). The sample shows a small crystalline melt with a peak at 60° C., followed by a broad exotherm beginning at about 200° C. The bulk sample is heated again at 235° C. for an additional 3 hours. Again a sample is removed and analyzed by DSC. The analysis indicates a very small crystalline melt with a peak at 60° C., followed by a low intensity exotherm beginning at about 230° C. The bulk sample is heated again to 265° C. for 45 minutes. Analysis of this sample indicates no crystalline melt and no exothermic activity up to and including 325° C., with the emergence of an endothermic glass transition (Tg) at 143° C.

EXAMPLE 2

Polymerization of 4,4'-Bis(Trifluorovinyloxy)Biphenyl in Solution

The monomer, 4,4'-bis(trifluorovinyloxy)biphenyl, (60.0 g, 0.173 mole) is placed in a 1 liter 3-necked round bottom flask with 75 ml of perfluorotetradecahydrophenanthrene (Multifluor® APF 215 commercially available from Air Products). The flask is fitted with a mechanical stirrer and a nitrogen padded reflux condenser. After purging the flask thoroughly with nitrogen, the mixture is stirred and heated to reflux. Initially, upon heating the melted monomer is not miscible with the solvent, but as the temperature rises the two phases become homogeneous. After stirring at reflux for approximately 45 minutes, a polymer phase separates; and, after stirring at reflux for a total of 3 hours, the phase separated polymer becomes viscous enough to seize the stirring shaft. The cooled polymer is removed from the flask and evaporated under high vacuum (approximately 0.50 torr) at about 220° C. for 3 hours to remove residual solvent. A portion of this polymer is compression molded at 250° C. to provide a light yellow, transparent flexible plastic film. Another portion is dissolved in tetrahydrofuran and placed in an evaporating dish to make a solvent-cast film. After the solvent is evaporated overnight, a light yellow thin film is peeled from the dish. This sample exhibits excellent flexibility and transparency.

An IR spectrograph of the film has the following peaks (cm$^{-1}$): 1601, 1490 (indicating aromatic double bonds); 1302, 1194-1115 (indicating carbon-oxygen and carbon-fluorine bonds), 818 (indicating aromaticity). DSC analysis of this polymer indicates a Tg transition at 148° C.

Dynamic mechanical analysis (DMS) gives a Tg value of 170°, and gel permeation chromatography (GPC) indicates a weight average molecular weight of 85,000 as standardized against polystyrene.

Dielectric constant and dissipation factor measurements performed on this polymer give the following results:

| Frequency (kHz) | Dielectric Constant | Dissipation Factor |
|---|---|---|
| 1.0 | 2.58 | 0.0007 |
| 10.0 | 2.57 | 0.0004 |
| 1000.0 | 2.55 | 0.0004 |

Examples 1 and 2 illustrate two types of polymerization of 4,4'-bis(trifluorovinyloxy)biphenyl. It is notable that the properties of each are roughly similar, with slightly more discoloration taking place in the bulk polymerization (according to the procedures of Example 1).

EXAMPLE 3

Preparation and Polymerization of 9,9-Bis(4'-[Trifluorovinyloxy]Phenyl)Fluorene Into a 2 liter 5-necked round bottom flask fitted with a mechanical stirrer, Dean-Stark trap topped with a nitrogen padded reflux condenser and a thermocouple attached to a temperature controller, are placed DMSO (650 ml) and toluene (200 ml). While the stirred solution is purged with nitrogen, 9,9-bis(4'-hydroxyphenyl)fluorene (200.0 g, 0.57 mole) is added to the flask. While purging with nitrogen continues, potassium hydroxide (85% pellets, 77.5 g, 1.17 mole) is added all at once, and the mixture is heated to 100° C. with constant stirring. After two hours, the temperature is increased until the solution begins to reflux (130° C.). Water is removed by azeotropic distillation for 24 hours. The Dean-Stark trap is replaced by a Soxhlet extractor containing anhydrous sodium sulfate, and the toluene is refluxed through the Soxhlet for 5 hours. A small amount of toluene (60 ml) is then removed by simple distillation. Then the reactor is cooled to 35° C. Addition of 1,2-dibromotetrafluoroethane (315 g, 1.21 mole) via dropping addition funnel is then maintained at a rate that keeps the reaction temperature at 35°-38° C. When the addition is complete, the mixture is heated at 50° C. for 8 hours, then cooled to room temperature with constant stirring. The mixture is filtered, and the precipitate is washed twice with acetone. The filtrates are combined and evaporated thoroughly. The residue from the evaporation is washed with water to remove residual potassium bromide (KBr). After the residue is air dried for 24 hours, it is purified by column chromatography (on neutral alumina, using hexane eluent) to provide as product, 9,9-bis(4'-[2''-bromotetrafluoroethoxy]phenyl)fluorene (331.4 g, 0.468 mole, 82% yield), melting point 157°-158° C.

The LC/MS spectrum has peaks at: m/e: 710 (53 0%); 709 (34.0%): 708 (100.0%); 707 (23.3%); 706

(49.8%): 513 (28.4%); 511 (28.5%); 438 (12.8%); 437 (52.4%): 436 (14.7%): 435 (55.8%): 355 (15.7%): 290 (33.9)%: 289 (19.5%); 239 (35.9%): 228 (36.2%); 227 (38.9%); 226 (47.3%): 202 (27.7%); 157 (47.2%); 131 (27.6%): 129 (23.1%).

The product from the above reaction (18.85 g, 0.027 mole) is combined with freshly activated granular zinc (5.00 g, 0.076 mole) in glyme and heated at reflux overnight. After cooling, the reaction mixture is decanted and centrifuged to remove suspended zinc salts. The solvent is removed by vacuum evaporation, and the residue is purified by column chromatography on neutral alumina using hexane as an eluent to provide as product 9,9-bis(4'-trifluorovinyloxyphenyl)fluorene (5.55 g, 0.011 mole, 40% yield), melting point 115°–116° C.

The LC/MS spectrum has peaks at: m/e: 511 (29.3%): 510 (91.9%); 337 (37.2%): 316 (16.1%); 315 (19.7%): 313 (12.8%); 241 (15.5%); 240 (52.8%): 239 (100.0%): 237 (15.6%): 207 (14.1%): 158 (28.7%); 157 (53.1%); 155 (14.4%); 150 (28.8%); 145 (18.3%); 144 (16.5%); 120 (15.1%).

Into a 50 ml round bottom flask fitted with a nitrogen padded reflux condenser, mechanical stirrer and a thermocouple attached to a temperature controller are placed 9,9-bis(4'-trifluorovinyloxyphenyl)fluorene (3.0 g, 0.0059 mole) and diphenyloxide (5.0 ml). The mixture is stirred and heated to reflux (255° C.) for 22 hours. The diphenyloxide (DPO) solvent is evaporated under high vacuum on a 100 milliliter Kugelrohr bulb to bulb apparatus (0.03 mm, 165° C.) to provide the polymer product, which is dissolved in methylene chloride and cast into a thin film.

Gel permeation chromatography analysis of the polymer indicates a weight average molecular weight of 135,000 as standardized against polystyrene.

DSC analysis indicates a Tg transition at 224° C.

Example 3 illustrates preparation and polymerization of of 9,9-bis(4,4'-trifluorovinyloxyphenyl)fluorene. It is notable that the resulting polymer, which is polymerized in DPO, attains a high molecular weight and forms a solvent cast film with good physical properties such as flexibility.

EXAMPLES 4–9

Preparation and Polymerization of a Variety of Perfluorocyclobutane Ring-Containing Polymers The procedure outlined in Example 3 is repeated for each of the indicated starting materials, except for the changes indicates in Table I and adjustments in amounts to maintain the stoichiometry of Example 3, to produce the indicated monomers of the structure:

$$CF_2=CF-O-R-O-CF=CF_2$$

Wherein R is given in Table 1

TABLE I

Preparation of Monomers

| EX. NO. | STARTING MATERIAL | R | Changes in procedure |
|---|---|---|---|
| 4 | Resorcinol | 1,3-Phenylene | Tetraglyme is used in second step. Product is distilled directly from reaction mixture under vacuum. *3-(1',1',2',2'-tetrafluoroethoxy)-trifluorovinyloxybenzene and 1,3-bis(1',1',2',2'-tetrafluoro-ethoxy)benzene are isolated as by products and identified by GC/MS spectra consistent with those compounds. |
| 5 | 4,4'-dihydroxy-biphenyl | 4,4'-Biphenyl | See Example 1 |
| 6 | 4,4'-thiodiphenol | 4,4'-Thiodiphenyl | Tetraglyme is used in second step, removed by diluting with methylene chloride and washing with water. |
| 7 | Bisphenol A | Isopropyl-2,2-diphenylene | |
| 8 | Hexafluorobisphenol A (bisphenol AF) | Hexafluoroisopropyl-2,2-diphenylene | |
| 9 | 9,9-bis(4'-hydroxyphenyl)fluorene | 9,9-bis(4'-phenylene)fluorene | See Example 3 |

The data in Table I shows that a variety of perfluorovinyl monomers are prepared by processes within the scope of the invention.

The procedure outlined in Example 2 is repeated for each of the monomers in Table I, except for the changes in procedure indicated in Table II to produce polymers from the indicated monomers. The properties of these polymers are given in Table II.

TABLE II

Properties of Thermoplastic Polymers

| Ex. | R | Tg (°C.) | Dielectric Constant 10 kHz | Dissipation Factor 10 kHz | Wt. Ave. Molecular Weight |
|---|---|---|---|---|---|
| 4 | 1,3-Phenylene | 32° | 2.41 | — | 41,400 |
| 5 | 4,4'-Biphenyl | 170° | 2.57 | 0.0004 | 85,000 |
| 6 | 4,4'-Thiodiphenyl | 78° | 2.62 | 0.0005 | 42,500 |
| 7 | Isopropyl-2,2-diphenylene | 98° | — | — | 50,700 |
| 8 | Hexafluoroiso-propyl-2,2-diphenylene | 125° | — | — | 23,500 |
| 9 | 9,9-bis(4'-phenylene)fluorene (prepared in diphenyloxide) | 224° | — | — | 135,000 |

The data in Table II shows that a variety of perfluorocyclobutane ring-containing polymers are prepared by processes within the scope of the invention.

EXAMPLE 10

Preparation of
1,1,1-Tris(4'-Trifluorovinyloxyphenyl)Ethane and Bulk Polymerization thereof with
4,4'-Bis(Trifluorovinyloxy) Biphenyl A 1 liter 5-necked round bottom flask is fitted with a mechanical stirrer, a Dean-Stark trap topped with a nitrogen padded reflux condenser, and a thermocouple attached to a temperature controller. A mixture of DMSO (450 ml), toluene (150 ml), and 1,1,1-tris(4'-hydroxyphenyl)ethane (55.1 g, 0.18 mole) is added to the flask under nitrogen purge. After stirring for 15 minutes under a vigorous nitrogen purge, potassium hydroxide (85% pellets, 80.0 g, 1.2 mole) is slowly added to the reaction flask. The mixture is then stirred at reflux for 48 hours with azeotropic removal of water. The resulting suspension is cooled to 35° C. in an ice bath and 1,2-dibromotetrafluoroethane (155 g, 0.60 mole) is added at a rate that maintains a temperature of 30°-35° C. When the addition is complete, the mixture is heated to 50° C. with continuous stirring for 3 hours. After filtration, the solvents are removed by heating under vacuum on a rotary evaporator. The brown residue is purified by column chromatography on neutral alumina using hexane as eluent to provide as product 1,1,1-tris(4'-[2''-bromotetrafluoroethoxy]phenyl)ethane (18.3 g, 0.022 mole, 12% yield).

Identity of the product is confirmed by a GC/MS spectrum, the following peaks: m/e: parent ions m/e 840-842-844-846 (ratio 1:3:3:1) too heavy to detect. Structure determined from fragmentation: 573 (32.3%); 571 (58.3%); 569 (31.5%) indicating parent-PhOCF$_2$CF$_2$Br]). 299 (58.1%): 297 (52.7%): 279 (32.3%); 28 (43.5%); 227 (31.5%): 226 (36.0%): 215 (59.5%): 181 (82.1%): 179 (100.0%): 165 (50.3%): 152 (43.7%); 131 (47.1%): 129 (50.4%): 100 (38.8%).

Into a 500 ml 5-necked flask fitted with a mechanical stirrer, a reflux condenser, and a thermocouple attached to a temperature controller is placed freshly activated granular zinc (4.3 g, 0.066 mole) and 25 ml dry diglyme. This mixture is stirred and heated to 110° C. under nitrogen while the product from the above reaction (18.0 g, 0.021 mole) is dissolved in 21 ml diglyme and added dropwise. The resulting mixture is stirred at 115° C. for 3 hours, then cooled and filtered. The filtrate is evaporated at 60° C. under vacuum to remove the diglyme, and the residue is purified by column chromatography on neutral alumina using hexane as eluent to provide the product 1,1,1-tris(4'-trifluorovinyloxyphenyl)ethane (9.98 g, 0.018 mole, 87% yield).

The GC/MS spectrum has the following peaks: m/e: 546 (3.2%): 531 (44.0%): 434 (17.9%): 373 (24.4%); 276 (16.9%); 240 (28.1%): 239 (73.9%); 199 (19.3%); 178 (100.0%); 177 (17.8%); 176 (25.4%); 163 (17.3%); 152 (31.9%); 151 (17.8%); 127 (20.3%); 126 (28.7%); 120 (39.1%); 119 (70.3%); 118 (25.6%); 113 (27.3%); 107 (18.8%); 102 (31.7%); 77 (15.9%); 76 (29.5%).

This example illustrates preparation of a trifunctional monomer, 1,1,1-tris(4'-trifluorovinyloxyphenyl)ethane. This monomer is useful alone or mixed with a bifunctional monomer to produce a crosslinked perfluorocyclobutane polymer.

A mixture of 4,4'-bis(trifluorovinyloxy)biphenyl (as prepared in Example 1) (4.50 g, 0.013 mole) and the 1,1,1-tris(4'-trifluorovinyloxyphenyl)ethane (0.79 g, 0.0014 mole) are combined in a 100 ml single necked round bottomed flask topped with a nitrogen padded reflux condenser. The flask is purged thoroughly with nitrogen, and the mixture is heated without stirring. After reaching a temperature of 200° C., the mixture sets into a rigid plastic within 15 minutes. This material is then cured an additional 40 minutes at 220° C.; then the heat is removed. The resulting plastic is rigid, inflexible and does not dissolve in tetrahydrofuran (THF) or methylene chloride, but swells into a gel in these solvents.

DSC analysis (25°-350° C., 20° C./min.) of this polymer sample shows a slight endothermic event at 125° C. followed by a broad exotherm beginning at about 210° C., indicative of an incompletely cured polymer. After this sample is cured during the first DSC scan, a second scan is run which clearly indicates a Tg transition at 151° C. and no subsequent exothermic activity at higher temperatures.

Example 10 illustrates preparation of 1,1,1-tris(4'-trifluorovinyloxyphenyl)ethane and copolymerizaton thereof 4,4'-bis(trifluorovinyloxy)biphenyl therewith. The resulting polymer is stiff and brittle, as well as insoluble, compared to the thermoplastic of Example 2, prepared from 4,4'-bis(trifluorovinyloxy) biphenyl alone, which is flexible and soluble in THF and methylene chloride.

EXAMPLE 11

Bulk Polymerization of
4,4'-Bis(Trifluorovinyloxy)Biphenyl with Subsequent Addition of
1,1,1-Tris(4'-Trifluorovinyloxyphenyl)Ethane Monomer 4,4'-bis(trifluorovinyloxy)biphenyl (16.2 g, 0.047 mole) is placed in a 500 ml round bottom flask along with a magnetic stirring bar. A nitrogen padded reflux condenser is placed on the flask, and the monomer is heated at 200°-205° C. with stirring for 20 minutes, to form a low molecular weight polymer resembling a thick fluid at 200° C. The fluid is allowed to cool to room temperature where it sets into a brittle glass. The glass is dissolved in methylene chloride and 1,1,1 tris(4'-trifluorovinyloxyphenyl)ethane (0.51 g, 0.00094 mole) is added to the solution. The methylene chloride is evaporated and the residue is dried and devolatilized on a Kugelrohr bulb to bulb apparatus at 120°-140° C. and 0.20 torr pressure. While still hot, the fluid mixture is poured into a mold and cured on a hot press at 250° C. and 20,000 psi for one hour. The mold is removed from the press and cooled. A coupon is removed from the mold. The coupon is a strong and flexible plastic, and does not dissolve in THF but swells into a gel therein.

DSC analysis of this crosslinked polymer sample indicates a Tg value of 149° C., with no subsequent thermal activity up to and including 350° C.

Example 11 illustrates polymerizaton of 4,4'-bis(trifluorovinyloxy)biphenyl with subsequent addition of 1,1,1-tris(4'-trifluorovinyloxyphenyl)ethane. It is notable that crosslinked polymers are prepared either by copolymerizing difunctional and multi-functional monomers, as in Example 10, or by combining a multifunctional monomer with a low molecular weight polymer containing trifluorovinyl end groups as in Example 11.

EXAMPLE 12

Preparation of 1,4-Bis(Trifluorovinyl)Benzene and Bulk Polymerization Thereof A 5 liter 3-necked round bottom flask is fitted with a mechanical stirrer, a nitrogen padded reflux condenser and a rubber septum. Glyme (100 ml) and activated zinc granules (11.50 g, 0.18 mole) are added to the flask along with a magnetic stirring bar. The flask is then purged with nitrogen for 15 minutes, after which time iodotrifluoroethylene (20.3 g, 0.098 mole) is added slowly via syringe through the septum. After 20 minutes of stirring the mixture begins to turn brown and get warm. After 2 hours a white precipitate begins to form. After stirring is continued without heat for 4 hours, the flask is opened under a slow nitrogen purge and 1,4-diiodobenzene (16.0 g, 0.0485 mole) is added along with palladium tetrakis(triphenylphosphine) (0.57 g, 0.00049 mole). The mixture is stirred overnight, resulting in the formation of a large amount of suspended solid. The reaction is allowed to stir an additional 24 hours, after which it is filtered, and the precipitate is washed with hexane (3 times with 50 ml each wash). The filtrates are combined and evaporated at 30° C. on a rotary evaporator to provide a residue which is purified by column chromatography (neutral alumnia, hexane eluent) to give 7.50 g of $CF_2=CF-Ph-CF=CF_2$ as product (0.0315 mole, 65% yield). This product is analysed by GC/MS and gives the following spectrum: m/e: 238 (100%): 188 (12.0%); 187 (46.4%): 169 (92.0%): 138 (18.8%): 99 (16.3%); 81 (12.3%): 69 (30.1%). The material is found to be air sensitive, fuming acid gasses if left exposed to oxygen.

This example illustrates preparation of an aromatic monomer having two perfluorovinyl groups directly attached to the aromatic ring and illustrate the use of iodotrifluoroethylene in preparation of a monomer. This preparation proceeds via a one pot synthesis to give good yields of the monomer.

It is noted that when a sample of this material is stored for 10 hours or more in contact with air that a highly mobile gel is formed along with the evolution of acid fumes. This observation is believed to be indicative of formation of acyl fluorides and fluoride ions, and of addition polymerization (rather than cyclization) catalyzed by the fluoride ion. The result of such storage in contact with air differs from the following product in that only a very low molecular weight gel is formed, with a high degree of crosslinking taking place in the gel matrix.

Monomer 1,4-bis(trifluorovinyl)benzene (1.00 g, 0.0042 mole) is placed in a 100 ml round bottom flask with a magnetic stir bar and purged with nitrogen. The neat monomer is heated to about 80° C. with slow stirring. In 10 minutes the monomer sets into a hard glassy polymer which is not soluble in THF or methylene chloride, but which turns brown and fumes acid gasses when left exposed to air overnight. This observation suggests that a low molecular weight polymer is formed and contains unreacted trifluorovinyl groups which are still air sensitive.

Example 12 illustrates polymerization of an aromatic monomer having two perfluorovinyl groups directly attached to the aromatic ring, which polymerization proceeds in a very short time and without the need of solvents.

EXAMPLE 13

Solution Polymerization of 1,4-Bis(Trifluorovinyl)Benzene

Monomer 1,4-bis(trifluorovinyl)benzene (1.00 g, 0.0042 mole) is combined in a 100 ml round bottom flask with 2.0 g of perfluorotetradecahydrophenanthrene (Multifluor® APF-215 commercially available from Air Products) and a magnetic stirrer. The flask is topped with a nitrogen padded reflux condenser. When the mixture is purged with nitrogen, it is heated to reflux with stirring. After 10 minutes, a crystalline precipitate is formed. This precipitate is isolated by filtration followed by vacuum drying.

The material is insoluble in THF or methylene chloride. A powder is formed by crushing the polymer precipitate in a mortar and pestle. Analysis of the powder by DSC indicates two small exothermic events, one at 180°–240° C., the other at 320°–380° C. leading into decomposition.

Example 13 illustrates solution polymerization of an aromatic monomer having two perfluorovinyl groups directly attached to the aromatic ring. This polymerization proceeds very quickly at higher temperatures and in the presence of inert solvents such as that used above.

EXAMPLE 14

Preparation and Polymerization of 4,4'-Bis(Trifluorovinyl)Biphenyl

A 1 liter 5-necked round bottom flask is fitted with a mechanical stirrer, a nitrogen padded reflux condenser and a rubber septum. Dry glyme (300 ml) and activated zinc granules (50.8 g, 0.395 mole) are added to the flask as it is purged thoroughly with nitrogen. Then iodotrifluoroethylene (100.0 g, 0.48 mole) is added to the flask all at once, and the mixture is stirred continuously under nitrogen for 5 hours. 4,4'-Diiodobiphenyl (97.0 g, 0.24 mole) is added to the flask along with nitrogen purged dimethylformamide (DMF) (300 ml) and palladium tetrakis(triphenylphosphine) (4.35 g, 0 0038 mole). The mixture is stirred at room temperature.

After 24 hours, a GC/MS of the mixture allows identification of all the reaction components. After 72 hours, the reaction seems to stop proceeding while excess diiodobiphenyl remains: another batch of iodotrifluoroethylene (25.0 g, 0.12 mole) is reacted with zinc in THF and added to the reaction mixture along with 1.0 g of palladium tetrakis(triphenylphosphine) catalyst. The reaction is allowed to stir an additional 12 hours, then is removed and evaporated to dryness under high vacuum on a rotary evaporator. Residue from evaporation is added to a 3 fold volumetric excess of water. A heavy precipitate is formed which is filtered and air dried on a vacuum funnel. The precipitate is dissolved in THF and filtered. The resulting filtrate is coated on silica gel by adding the silica gel to the THF solution and evaporating to dryness. This silica gel is then eluted on a short silica gel column using hexane as eluent to remove the colored material from the product. A fine white crystalline material remains after evaporation of the hexane. This crystalline material is then chromatographed again carefully on an alumina column using hexane as an eluent. The first band to elute from the column is the desired monomer product $CF_2=CF-Ph-Ph-CF=CF_2$. A total of 44.2 g of product is recovered (58.7% yield).

The crystalline product has a melting point of 83°–84.5° C.

Analysis by GC/MS gives the following mass spectral data for this product: m/e: 314 (100.0%): 263 (13.4%): 243 (14.9%): 69 (13.0%).

DSC analysis of this monomer shows a sharp endotherm at about 82° C. followed closely by a broad exotherm corresponding to cyclization of the trifluorovinyl groups beginning at about 98° C. A second exothermic event begins at about 300° C. leading into decomposition at >400° C. The monomer is also oxidatively unstable, as indicated by turning brown and releasing acid fumes when allowed to stand in air.

Example 14 illustrates preparation of another aromatic monomer having two perfluorovinyl groups directly attached to the aromatic ring. Because of the crystalline nature of this product, a gel is not formed on standing, although oxidative decomposition does appear to evolve acid gasses at a somewhat slower rate than the product of Example 12.

A sample of the 4,4'-bis(trifluorovinyl)biphenyl (1.6 g, 0.005 mole) and fresh anhydrous DMF (5.0 ml) are added to a 100 ml single necked round bottom flask with a thermometer port along with a magnetic stirrer. The flask is topped with a nitrogen padded reflux condenser and stirring is begun as nitrogen is allowed to pass out of the thermometer port. After 5 minutes of nitrogen purge, a thermocouple is placed in the thermometer port and heating is begun. The solution is heated to 40° C. for 4 hours with no apparent reaction. The temperature is then raised in 10° C. increments, holding each new temperature for at least 45 minutes before proceeding to the next higher temperature. After the mixture is stirred at 130° C. for 2 hours with no apparent change, the temperature is raised to 135° C. and left to stir overnight. The next morning the mixture is somewhat darker and noticeably higher in viscosity. The temperature is then raised to 140° C. for 9 hours, after which the mixture becomes very thick, at which time heating and stirring are stopped. A sample of the viscous liquid is removed and evaporated to dryness under vacuum, leaving a brittle crystalline powder. This powder dissolves in methylene chloride but does not filter through a 5 micron filter. Only a few drops of filtrate are recovered, and this filtrate is analyzed by gel permeation chromatography as standardized against polystyrene. As recovered by this method, the soluble portion of the polymer has a weight average molecular weight of 41,600.

DSC analysis of the crystalline polymer shows no thermal activity up to and including 400° C., with apparent decomposition beginning at about 420° C. All of the polymer samples prepared from this monomer are still air sensitive, as is evidenced by fuming of acid gasses after standing in air.

Example 14 illustrates polymerization of an aromatic monomer having two perfluorovinyl groups directly attached to the aromatic ring. This example also illustrates that careful temperature control may be employed to control the rate and extent of polymerization.

EXAMPLE 15

Preparation of a Fluid Polymer of 1,3-Bis(Trifluorovinyloxy)Benzene and 3-Trifluorovinyloxy-1',1',1'-Trifluorotoluene To synthesize m-trifluorovinyloxy-1',1',1'-trifluorotoluene, DMSO (400 ml), toluene (140 ml), and 3-trifluoromethylphenol (81.0 g, 0.50 mole) are placed in a 1 liter 3-necked flask equipped with a mechanical stirrer, a Dean-Stark trap and a thermocouple attached to a temperature controller. The stirred solution is purged of oxygen by placing a dip tube below the surface of the solution and allowing nitrogen to be blown into the solution for 15 minutes. Potassium hydroxide (85% pellets, 33.7 g, 0.51 mole) is added to the flask all at once, and a line to supply nitrogen is attached to a reflux condenser which is placed on top of the Dean-Stark trap. The mixture is then heated to 145° C. and water is removed azeotropically. When water ceases to collect in the Dean-Stark trap, the temperature of the reaction is increased to 155° C. and 100 ml of toluene is removed by distillation, leaving a reaction mixture in the flask.

The reaction mixture is cooled to room temperature, and 1,2-dibromotetrafluoroethane (132.0 g, 0.51 mole) is added slowly using a dropping addition funnel. The mixture is heated to 55° C. for 5 hours, then allowed to cool to room temperature. After the suspended solids have settled, the liquid is decanted away from the precipitate and is retained as a mixture of product in DMSO, which is added to a 3 times volumetric excess of water in a separatory funnel and shaken vigorously. The product forms a separate, lower layer at the bottom of the funnel and is removed. This crude product (lower layer) is washed again with 500 ml of water. After drying the washed lower layer over anhydrous magnesium sulfate, the crude product is fractionally distilled. The product, m-(2-bromotetrafluoroethoxy)-1',1',1'-trifluorotoluene (169°–171° C., 150 torr) gives the following mass spectral data: m/e: 342 (20.1%): 340 (19.8%): 323 (7.9 %); 321 (7.2 %): 211 (25.6 %): 145 (100.0%).

The product of the above reaction (56.0 g, 0.164 mole) is combined with granular zinc (12.0 g, 0.18 mole) in dry tetraglyme and stirred at 115° C. for 6 hours to form a reaction mixture. The mixture is cooled to room temperature, and a distillation head is placed on the reaction flask. The product is then distilled directly out of the crude reaction mixture (108°–110° C., 150 torr) to give 40.5 g of the product, m-trifluorovinyloxy-1',1',1'-trifluorotoluene, which is 78% pure by GC analysis, with the remainder of the product being the by-product m-(1,1,2,2,-tetrafluoroethoxy)-1',1',1'-trifluorotoluene.

The product gives the following mass spectral data: m/e: 242 (52.3%): 223 (12.3%); 195 (14.2%): 145 (100%): 125 (18.3%): 95 (30.6%).

A mixture is prepared from 1.25 ml of 1,3-bis(trifluorovinyloxy)benzene (as prepared in Example 4) and 8.75 ml of 3-trifluorovinyloxy-1',1',1'-trifluorotoluene to make a total of 10 ml. This mixture is placed in a 50 ml round bottom flask fitted with a nitrogen padded reflux condenser and is refluxed under nitrogen for 20 hours.

The resulting product is analyzed by GC/MS and found to be a mixture of hexafluorocyclobutane products whose major components are 1,2-bis(3'-trifluoromethylphenoxy) hexafluorocyclobutane and 1,3-bis(2'-[3'''-trifluoromethylphenoxy] hexafluorocyclobutyl)phenyl ether (having two perfluorocyclobutane rings), with a trace amount of 1,2-bis(3'-[2'''-{3''''-trifluoromethylphenoxy}hexafluorocyclobutyloxyphenyl) hexafluorocyclobutyl ether (having three perfluorocyclobutane rings). By vacuum distillation two fractions are collected.

The first fraction contains primarily monoperfluorocyclobutane material consisting of two isomers (cis and trans 1,2-substituted hexafluorocyclobutane) with similar mass spectra (given for one isomer only): m/e: 484 (20.2%): 465 (12.9%); 273 (29.2%); 242 (30.1%); 207 (11.2%); 195 (13.0%); 145 (100.0%).

The second fraction contains predominantly diperfluorocyclobutane material, consisting mainly of three isomers (cis-cis, cis-trans, and trans-trans) of 1,2-substituted hexafluorocyclobutanes, and small amounts of four isomers of a product containing one 1,2-substituted hexafluorocyclobutane ring and one 1,3-substituted hexafluorocyclobutane ring (cis-1,2 cis-1,3; cis-1,2 trans-1,3: trans-1,2 cis-1,3; and trans-1,2 trans-1,3). All seven products give roughly the same peaks in their mass spectra in differing intensities. The following mass spectral data is for the first product isomer to elute from the gas chromatography (GC) column, and corresponds to one of the three main isomers of two perfluorocyclobutane rings: m/e: 754 (36.4%); 593 (12.5%); 492 (14.1%): 415 (21.9%); 273 (27.7%): 242 (39.1%): 195 (21.5%); 173 (23.4%): 145 (100.0%): 126 (28 5%): 95 (23.1%): 92 (34.7%); 76 (57.6%): 64 (27.3%).

The second fraction also contains a small amount of material containing three perfluorocyclobutane rings, consisting of six isomers (cis-cis-cis, cis-cis-trans, cis-trans-cis, cis-trans-trans, trans-cis-trans, and trans-trans-trans) of 1,2-substituted hexafluorocyclobutanes. Because of the small amount of this product present in the mixture, the corresponding products containing one or more 1,3-substituted hexafluorocyclobutane rings are not detected. The mass spectra of the six isomers showed roughly the same peaks in slightly differing intensities. The following mass spectral data is from the first product isomer of triperfluorocyclobutane material to elute from the GC column: m/e: 1024 (21.6%): 593 (16.3%): 492 (35.5%): 415 (17.6%); 281 (16.2%); 273 (16.4%); 242 (26.0%): 208 (15.9%): 207 (71.9%): 145 (100.0%): 92 (19.7%); 76 (26.8%).

In all cases, the primary products of cyclization are 1,2-substituted hexafluorocyclobutanes, with small amounts (1-2%) of 1,3-substituted hexafluorocyclobutanes observable by GC/MS, (except for the tri-perfluorocyclobutane material, of which only trace amounts are seen) the two being distinguished by a small peak at m/e=100, corresponding to a fragment of $CF_2=CF_2$ present in the mass spectra of the 1,2-substituted hexafluorocyclobutanes which is absent in the 1,3-substituted products. Absolute configurations of the different isomers are not assigned.

This example shows that a compound containing one trifluorovinyl group can be combined with a compound containing two trifluorovinyl groups, the mixture then being heated to cause cyclization of the trifluorovinyl groups to provide a fluid containing perfluorocyclobutane groups. Such fluids are of the type useful as low dielectric hydraulic fluids or lubricants.

EXAMPLE 16

Preparation of a Fluid Polymer of 1,3-Bis(Trifluorovinyloxy)Benzene,3-(1',1',2',2',Tetrafluoroethoxy)Trifluorovinyloxybenzene and 1,3-Bis(1',1',2',2'-Tetrafluoroethoxy)Benzene A mixture (25 ml) consisting of 1,3-bis(trifluorovinyloxy)benzene (as prepared in Example 4) (26%), 3-(1',1',2',2',tetrafluoroethoxy)trifluorovinyloxybenzene (54%), 1,3-bis(1',1',2',2'-tetrafluoroethoxy)benzene (as isolated in Example 4) (15%),and tetraglyme (5%) is placed in a 100 ml round bottom flask and heated at reflux under nitrogen for 5 hours. The resulting viscous oil is checked by GC and is found to contain unreacted 1,3-bis(1',1',2',2',-tetrafluoroethoxy)benzene and tetraglyme, as well as mixtures of isomers of heavy components. After removal of the light, unreacted components, two fractions are cleanly separated by fractional distillation and each is analyzed by GC/MS.

The first fraction is found to contain primarily 1,2-bis(3'-[1'',1'',2'',2''-tetrafluoroethoxy]phenoxy)hexafluorocyclobutane as two isomers (cis and trans substituted hexafluorocyclobutane) followed by small amounts (1-2% each) of two 1,3-substituted hexafluorocyclobutane products (cis and trans), all having roughly similar mass spectra. The following is the mass spectral data for the first isomer to elute from the chromatography column, and corresponds to one of the 1,2-substituted isomers: m/e: 580 (25.8%): 371 (11.3%): 321 (12.5%): 290 (23.4%): 270 (36.4%): 243 (69.9%): 193 (100.0%): 95 (96.4%): 92 (55.9%): 76 (26.7%): 64 (29.9%); 51 (21.9%).

The second fraction contains 1,3-bis(2'-[3''-{1''',1''',2''',2'''-tetrafluoroethoxy}phenoxy]hexafluorocyclobutyl)phenyl ether, primarily as three isomers of 1,2-substituted hexafluorocyclobutanes with a small amount of four isomers of the product with one 1,2-substituted and one 1,3-substituted hexafluorocyclobutane ring. The seven isomers all give roughly the same peaks in their mass spectra in differing intensities. The following mass spectral data is for the first isomer to elute from the GC column, and corresponds to one of the three main isomers of the product: m/e: 850 (24.7%): 540 (24.2%); 371 (41.5%); 321 (12.9%); 301 (16.4%); 290 (33.9%): 270 (74.4%): 243 (63.9%); 207 (24.1%): 193 (86.7%): 173 (14.8%); 95 (100.0%): 92 (63.2%), 76 (71.8%)64 (32.6%): 51 (15.5%).

This example shows that a compound containing one trifluorovinyl group may be combined with a compound containing two trifluorovinyl groups in a solvent, the resulting mixture being heated to cause cyclization of the trifluorovinyl groups Such fluids are of the type useful as low dielectric hydraulic fluids or lubricants.

EXAMPLE 17

Preparation of 2,5-Bis(2-Trifluoroethenyloxy)Hexane

Sodium hydride (16 5 g, 60% dispersion in oil, 0.41 mol) is transferred to an oven dried 2L 3-necked flask. Dry dimethyl formamide (DMF) (400 mL) is added via syringe and the flask is fitted with a stirrer, thermometer, and septum. The mixture is stirred and cooled in an ice bath as 2,5-hexanediol (17.78 g, 0.15 mol) dissolved in 50 mL of dry DMF is added slowly via syringe. The septum is replaced with a pressure-equalizing addition funnel, and the mixture is allowed to stir overnight. The mixture is cooled to −10° to −15° C. with a dry ice-/ethylene glycol bath, and 1,2-dibromotetrafluoroethane (TFDBE) (60 mL, 0.5 mol) is added dropwise to the stirring mixture. The temperature of the reaction is maintained at −10° to −8° C. After one equivalent has been added, foaming is observed, which is allowed to subside before addition of TFDBE is resumed. Some slight foaming is observed for the rest of the reaction. As the reaction approaches completion, large amounts of solid precipitate, which redissolve when the reaction is allowed to warm to 10° C.

The reaction mixture is partitioned between hexane and water. The hexane layer is washed with additional water to remove residual DMF, dried over magnesium sulfate, and concentrated to yield 63.15 g of orange oil. Volatile products are removed by vacuum distillation to yield 36.12 g of colorless oil, which is then chromatographed on alumina with hexane to yield 19.23 g of 2,5-bis(2-bromotetrafluoroethoxy)hexane (26.9% yield) and 5.42 g of 2-(2-bromotetrafluoroethoxy)-5-(1,1,2,2-tetrafluoroethoxy)hexane as confirmed by 19F NMR, 1H NMR and IR spectra of products 19F NMR: (TFA) $\delta$-10.2 (t, J=6 Hz), 8.8 (t, J=6 Hz) HNMR: (TMS) $\delta$1.32 (d, 6H, J=6 Hz), 1.63-1.90 (m, 4H), 4.20-4.78 (m, 2H).

Zinc (1.93 g, 30 mmol) and 2,5-bis(2-bromotetrafluoroethoxy)hexane (3.45 g, 7.25 mmol) are weighed into a dry 100 mL 3-necked flask. Dry glyme (25 mL) is added via syringe and the resulting mixture is stirred and heated to reflux under nitrogen for 5 hours. The mixture is partitioned between pentane and water. The pentane extracts are dried over magnesium sulfate and concentrated to yield 2 11 g of pale yellow oil. Infrared analysis of this oil indicates the presence of some carbonyl containing impurities. The oil is dissolved in pentane and flushed through a column of neutral alumina to yield, after concentration, 1.33 g (65.8% yield) of the desired product. The title product is identified by 19F NMR, 1H NMR, and IR spectra 19F NMR: (TFA) $\delta$46.2 (ddd, J=90 Hz, Jcis=78 Hz, JFH=2 Hz, OCF), 53.8 (d, J=78, =CF cis), 53.9 (d, J=90, =CF trans)1H NMR: (TMS) $\delta$1.31 (d, J=6 Hz, 6H), 1.55-1.90 (m, 4H), 3.80-4.40 (m, 2H) IR: ($CM^{-1}$) 1845 ($CF=CF_2$), 1290 (B,C-O), 1130 (B, C-O).

The material is analyzed by DSC, and exhibits an exotherm of 500 Joules per gram (J/g) at 107° C.

EXAMPLE 18

Preparation of Methyl 4-(2-Bromotetrafluoroethoxy)Benzoate, its Conversion to to 4-Trifluoroethenyloxybenzoic Acid and the Benzoyl Chloride, and Use of the Chloride to Chain Extend Polycarbonate Oligomers.

Methyl 4-hydroxybenzoate (304.3 g, 2 mol) is dissolved in 800 mL of methanol and is converted to the potassium salt by the slow addition of potassium hydroxide (132.02 g, 2 mol, 85% purity). The resulting mixture is stirred and cooled as necessary to maintain the temperature below 50° C. The solvent is then removed by rotary evaporation and the crystalline salt is dried under vacuum overnight at 140° C.

The dried salt is allowed to cool and transferred to an oven dried 2L flask under nitrogen. The flask is fitted with a mechanical stirrer, thermometer, heating mantle, condenser and pressure-equalizing addition funnel. Dry dimethylsulfoxide (DMSO) (550 g) is added and the mixture is stirred and warmed to 60° C. as 1,2-dibromotetrafluoroethane (537 g, 2.06 mol) is added slowly. (No appreciable reaction is observed at lower temperatures.) Reaction temperature is maintained at 65°-70° C. for two hours after addition is complete. The mixture is then heated to 90° C. and allowed to cool overnight.

Product is isolated by extracting the mixture with 500 mL of water to remove salts and DMSO. The product separates as an orange oil which is washed with water to remove residual DMSO. (The upper aqueous layer is extracted with methylene chloride, and the methylene chloride solution is evaporated to yield about 40 g of product which is added to the rest of the product prior to the water washes.) The product (623 g) is distilled at 85° C./0.3 mm Hg to yield 561 g of colorless oil, 85% yield. The product is identified by 19F NMR, 1H NMR, and IR spectra.

To form a salt suitable for formation of the perfluorovinyl ether, another sample of methyl 4-(2-bromo-tetrafluoroethoxy)benzoate (66.25 g, 0.2 mol) is weighed into a 4-necked 500 mL round-bottomed flask fitted with a condenser, thermometer, mechanical stirrer, and heating mantle. Methanol (300 mL) and sodium hydroxide (8.05 g, 0.2 mol) are added to form a mixture which is stirred and heated to reflux for three hours. A sodium carboxylate forms and begans to precipitate early in the reaction and is gelled into an almost solid mass after 1.5 hours. The mass is allowed to settle overnight and the solvent is then removed by rotary evaporation.

The sodium carboxylate is dissolved in warm water. A warm solution of zinc acetate (26.35 g, 0.12 mol) in 40 mL of water is added to precipitate the carboxylate as the zinc salt. The salt slurry is then cooled, and the zinc salt is filtered from the solution and dried under vacuum to yield 65.6 g (94% yield).

The dried zinc salt is transferred to a dry 4-necked 500 mL round-bottomed flask containing zinc metal (10 mesh, 13.0 g, 0.198 mol). Dry glyme (160 mL) is added by a canula and the flask is fitted with a condenser, mechanical stirrer, and thermometer. The mixture is stirred and heated to reflux under nitrogen overnight. The mixture is acidified by the addition of 18 mL of concentrated HCl, concentrated by rotary evaporation, and then partitioned between methylene chloride and water. The methylene chloride solution of the acid is dried over magnesium sulfate, filtered and concentrated to yield 40.02 g of 4-trifluoroethenyloxybenzoic acid as white crystals (97.6% yield, m.p. 139°-140° C.). The product 4-trifluoroethenyloxybenzoic acid is identified by 19F NMR, 1H NMR, and IR spectra.

To form the 4-trifluoroethyloxybenzoyl chloride, 4-trifluoroethenyloxybenzoic acid (79.4 g, 0.36 mol) is transferred to a 1L round-bottomed flask. Dry methylene chloride (250 mL) is added, and the resulting mixture is stirred under nitrogen as oxalyl chloride (62.5 g, 0.49 mol) is added. The mixture is stirred overnight and then concentrated by rotary evaporation. The brown liquid is distilled at 60°-65° C./0.2 mmHg to yield 82.94 g of colorless liquid (97.4% yield). The product is identifed by 19F NMR, 1H NMR, and IR spectra.

To cap an oligomer, a low molecular weight polycarbonate oligomer (2000 MW) terminated with bisphenol A groups (7.5 g, about $7.8 \times 10^{-3}$ mol of phenolic OH) is weighed into a 100 mL flask with the trifluoroethenyloxybenzoyl chloride (1.84 g, $7.8 \times 10^{-3}$ mol). Dichloromethane (30 mL) is added to dissolve the oligomer, and the mixture is stirred as triethylamine (0.81 g, $8 \times 10^{-3}$ mol) is added via syringe. A fine white precipitate forms in the mixture almost immediately. Dichloromethane is added to dissolve the precipitate, forming a dichloromethane solution which is extracted with water to remove triethylamine hydrochloride. The dichloromethane solution is dried over 4A molecular sieves, and concentrated to yield 9.06 g (100 % yield) of oligomer capped with trifluoroethenyloxybenzoyl groups. Structure is verified by 19F NMR (trifluorovinyl ether pattern), 1H NMR (2 protons of the aromatic benzoate are shifted downfield to 8-8.3 ppm from the aromatic polycarbonate protons), and FT-IR (C=O stretch at 1739 cm$^{-1}$, distinct from the C=O stretch of polycarbonate at 1774 cm$^{-1}$).

A sample of the capped oligomer is heated to 300° C. in a DSC apparatus to effect chain extension. The sample is cooled and reheated to determine the Tg, which is observed at 140.4° C. (representative of high molecular weight polycarbonate). For comparison, a sample of the uncapped oligomer heated to 300° C., cooled, and reheated, exhibits a Tg of only 106.8° C. The increase of 33.6° C. in the Tg is attributed to the production of high molecular weight polycarbonate through the thermal cyclodimerization of the trifluorovinyl ether groups.

EXAMPLE 19

Reaction of 4,4'-Biphenol and Trifluorovinyloxybenzoyl Chloride

Dihydroxybiphenyl 0.7888 g, 0.00423 mole) is placed in a dry 250 ml round bottom flask with a magnetic stirring bar. The flask is capped with a rubber septum. Dry methylene chloride (25 ml) and trifluorovinyloxybenzoyl chloride as prepared in Example 18 (2.000 g, 0.00846 mole) are each added to the flask via syringe. The mixture is stirred as triethlyamine (0.86 g, 0.0085 mole) is added dropwise. The mixture is stirred at room temperature for 2 hours, then filtered. A white precipitate is obtained and washed several times with methylene chloride to remove residual triethlamine hydrochloride. A white crystalline product is obtained and has a melting point of 225°-228° C. Qualitative solubility tests indicate that this product is nearly insoluble in methylene chloride, acetone, acetonitrile, hexane, methanol, water and benzene, only slightly soluble in hot tetrahydrofuran, and moderately soluble in carbon tetrachloride.

Infrared analysis (using a potassium bromide (KBr) pellet) gives the following spectrum (reported in cm-1): 1830, indicative of a trifluorovinyl group; 1723, indicative of a benzoate ester; 1600 and 1495, indicative of aryl carbon-carbon double bond; 1315 and 1267, indicative of carbon-fluorine bonds.

Thermal analysis (DSC) of the monomer indicates a crystalline melt beginning at 223° C., followed immediately by a slight exotherm as the monomer undergoes polymerization. A second scan of the sample shows no thermal activity up to and including 350° C.

The melted monomer exhibits possible liquid crystalline behavior during it's short lived melt phase. As viewed under a cross-polarized light microscope, the melted monomer phase (at 230° C.) exhibits birefringence suggestive of liquid crystalline behavior, followed by rapid polymerization to a crystalline solid. This solid does not melt, but undergoes discoloration and apparent decomposition when heated in air at temperatures above 400° C.

EXAMPLE 20

Synthese of 1-Bromo-2,4-Bis(2-Trifluoroethenyloxy)Benzene from Resorcinol

Resorcinol (412.9 g, 3.75 mol) is dissolved in 1800 mL of DMSO and 670 mL of toluene to form a mixture in a 3-necked, 5L flask fitted with an overhead stirrer, moisture trap and condenser, and nitrogen sparge. The mixture is stirred and sparged with nitrogen as potassium hydroxide (495.1 g, 7.5 mol) is added in 5 g portions. The mixture is then heated to reflux to remove water by azeotropic distillation. After the water is removed, the mixture is cooled to 15° C. as 1,2-dibromotetrafluoroethane (2144 g, 8.25 mol) is added rapidly, and the mixture is stirred overnight. The mixture is then stirred and heated to 90° C. for three hours. The mixture is then cooled and diluted with an equal volume of water. The product separates as an oily lower layer, which is fractionally distilled under vacuum to yield 190.3 g of 1-(2-bromotetrafluoroethoxy)-3-(1,1,2,2-tetrafluoroethoxy)-benzene (3% yield), 895.5 g of 1,3-bis(2-bromotetrafluoroethoxy)benzene (51% yield), and 340.8 g of 1-bromo-2,4-bis(2-bromotetrafluoroethoxy)benzene (17% yield). The products are identified by 19F NMR, H NMR, and IR spectra.

1-Bromo-2,4-bis(2-bromotetrafluoroethoxy)benzene (18.06 g, 35 mmol) is added dropwise to a hot (110° C.) mixture of zinc (4.74 g, 72.5 mmol) in dry tetraglyme (20 mL). Product 1-bromo-2,4-bis(trifluoroethenyloxy)-benzene is fractioally distilled from the mixture under vacuum (95°-100° C./1 torr, 6.57 g, 59% yield). The product is identified by 19F NMR, H NMR, and IR spectra.

What is claimed is:

1. A compound having a structure represented by Formula I:

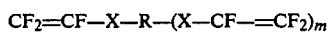

$$CF_2=CF-X-R-(X-CF=CF_2)_m$$

wherein R represents an unsubstituted or inertly substituted hydrocarbyl group; each X is independently selected from the group consisting of groups having at least one non-carbon atom between R and —CF=CF$_2$; and m is an integer of from 1 to about 3; wherein either R is an unsubstituted or inertly substituted aromatic group or X is selected from the group consisting of oxygen atoms, sulfur atoms, sulfoxide, sulfone, carbonyl, and thiocarbonyl groups.

2. The compound of claim 1 wherein X is selected from the group consisting of an oxygen atom, carboxylic and thiocarboxylic ester groups, phosphines, carbonyl and thio carbonyl groups: seleno: telluro: nitrido; silanediyl, trisilanediyl tetrasilanetetrayl, siloxanediyl, disiloxanediyl, trisiloxyl, trisilazanyl, or silylthio groups: boranediyl or methylboranediyl groups.

3. The compound of claim 1 wherein X is selected from the group consisting of oxygen atoms, sulfur atoms, sulfoxide, sulfone, carbonyl, thiocarbonyl and silanediyl groups.

4. The compound of claim 1 wherein each X is independently an oxygen atom, a sulfur atom, a sulfoxide group, or a sulfone group.

5. The compound of claim 3 wherein the X's are oxygen.

6. The compound of claim 4 wherein R is an unsubstituted or inertly substituted aromatic group.

7. The compound of claim 6 wherein R has from about 6 to about 25 carbon atoms.

8. The compound of claim 6 wherein the aromatic group is selected from the group consisting of biphenylene; phenylene; 9,9'-diphenylfluorene, oxydiphenylene; thiodiphenylene; 2,2-diphenylene propane; 2,2-diphenylene, 1,1,1,3,3,3-hexafluoropropane: 1,1-diphenylene-1-phenylethane; naphthalene: and anthracene.

9. The compound of claim 6 wherein each X is oxygen.

* * * * *